United States Patent
Kozloski et al.

(10) Patent No.: US 10,537,701 B2
(45) Date of Patent: Jan. 21, 2020

(54) ALLEVIATING MOVEMENT DISORDER CONDITIONS USING UNMANNED AERIAL VEHICLES

(71) Applicant: International Business Machines Corporation, Armonk, NY (US)

(72) Inventors: James R. Kozloski, New Fairfield, CT (US); Clifford A. Pickover, Yorktown Heights, NY (US); John J. Rice, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 558 days.

(21) Appl. No.: 15/202,032

(22) Filed: Jul. 5, 2016

(65) Prior Publication Data

US 2018/0008797 A1    Jan. 11, 2018

(51) Int. Cl.
  *A61M 21/00*    (2006.01)
  *B64C 39/02*    (2006.01)
  *B64D 47/02*    (2006.01)

(52) U.S. Cl.
  CPC .......... *A61M 21/00* (2013.01); *B64C 39/024* (2013.01); *B64D 47/02* (2013.01); *A61M 2021/0022* (2013.01); *A61M 2021/0027* (2013.01); *A61M 2021/0044* (2013.01); *B64C 2201/12* (2013.01)

(58) Field of Classification Search
  CPC .. A61M 2021/0005; A61M 2021/0027; A61M 2021/0044; A61M 2021/005; A61M 2230/60; A61M 21/00; A61N 5/0618; A61N 5/1048; B64C 39/024; B64C 2201/126

See application file for complete search history.

(56) References Cited

U.S. PATENT DOCUMENTS

2012/0259652 A1    10/2012   Mallon et al.
2015/0116316 A1    4/2015    Fitzgeral et al.
2016/0101856 A1    4/2016    Kohstall

FOREIGN PATENT DOCUMENTS

DE    102014215487 A1    2/2016

*Primary Examiner* — William H Matthews
(74) *Attorney, Agent, or Firm* — Cantor Colburn LLP; Anthony Curro (57) ABSTRACT

Aspects include a method, system and computer program product for alleviating an episode of a movement disorder condition for a patient. The method comprises deploying an unmanned aerial vehicle (UAV) to a location of a patient based on an occurrence of an episode of a movement disorder condition. A first gross sensory change stimulus is selected with a processor. The first gross sensory change stimulus is projected from the UAV. An attempt to alleviate the episode of the movement disorder condition is performed based at least in part on the projecting of the first gross sensory change stimulus from the UAV. The alleviating of the episode of the movement disorder condition is detected based on the gross sensory change stimulus from the UAV.

13 Claims, 10 Drawing Sheets

ALLEVIATING MOVEMENT DISORDER CONDITIONS USING UNMANNED AERIAL VEHICLES

BACKGROUND

The present invention relates generally to systems, methods and computer program products for use by a person having a movement disorder and, more specifically, to systems, methods and computer program products for using unmanned aerial vehicles for alleviating an episode of a movement disorder condition (e.g., a Freezing of Gait (FoG) episode in Parkinson's Disease).

Movement disorders are a broad category of disorders or syndromes that impact the health of a patient. These disorders, which include Parkinson's disease, Wilson's disease and peripheral neuropathy, for example, are neurologic syndromes in which either the patient exhibits an excess of movement or a paucity of voluntary and automatic movements, unrelated to weakness or spasticity. Other types of disorders having movement impairment that may also be categorized as a movement disorder include multiple sclerosis, chronic alcoholism, cerebellar damage, strokes and dementia with Lewy bodies (Alzheimer's disease). These disorders are sometime marked by temporary conditions or episodes, such as a frozen gait for example, which may require an intervention to alleviate or facilitate an end to the condition.

SUMMARY

Embodiments include a method, system and computer program product for alleviating an episode of a condition for a person having a movement disorder. The method comprises deploying an unmanned aerial vehicle (UAV) to a location of a patient based on an occurrence of an episode of a movement disorder condition. A first gross sensory change stimulus is selected with a processor. The first gross sensory change stimulus is projected from the UAV. An attempt to alleviate the episode of the movement disorder condition is performed based at least in part on the projecting of the first gross sensory change stimulus from the UAV. The alleviating of the episode of the movement disorder condition is detected based on the gross sensory change stimulus from the UAV.

Additional features are realized through the techniques of the present invention. Other embodiments and aspects of the invention are described in detail herein and are considered a part of the claimed invention. For a better understanding of the invention with the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features of embodiments of the invention are apparent from the following detailed description taken in conjunction with the accompanying drawings in which:

DETAILED DESCRIPTION

Embodiments of the present disclosure are directed to systems, methods and computer program products for monitoring, detecting and alleviating an episode of a condition for a person having movement disorder, such as Parkinson's disease. Embodiments of the present disclosure utilize an unmanned autonomous vehicle ("UAV") to monitor and evaluate the status of a patient and project or emit a gross sensory change stimulus in an attempt to alleviate an episode of a movement disorder condition (e.g., a Freezing of Gait (FoG) episode in Parkinson's Disease). Embodiments of the present invention further provide for monitoring of the effectiveness of gross sensory change stimulus in alleviating the episode of a condition and learning which stimulus are effective at alleviating the episode of a condition and under what circumstances.

Figure 1:
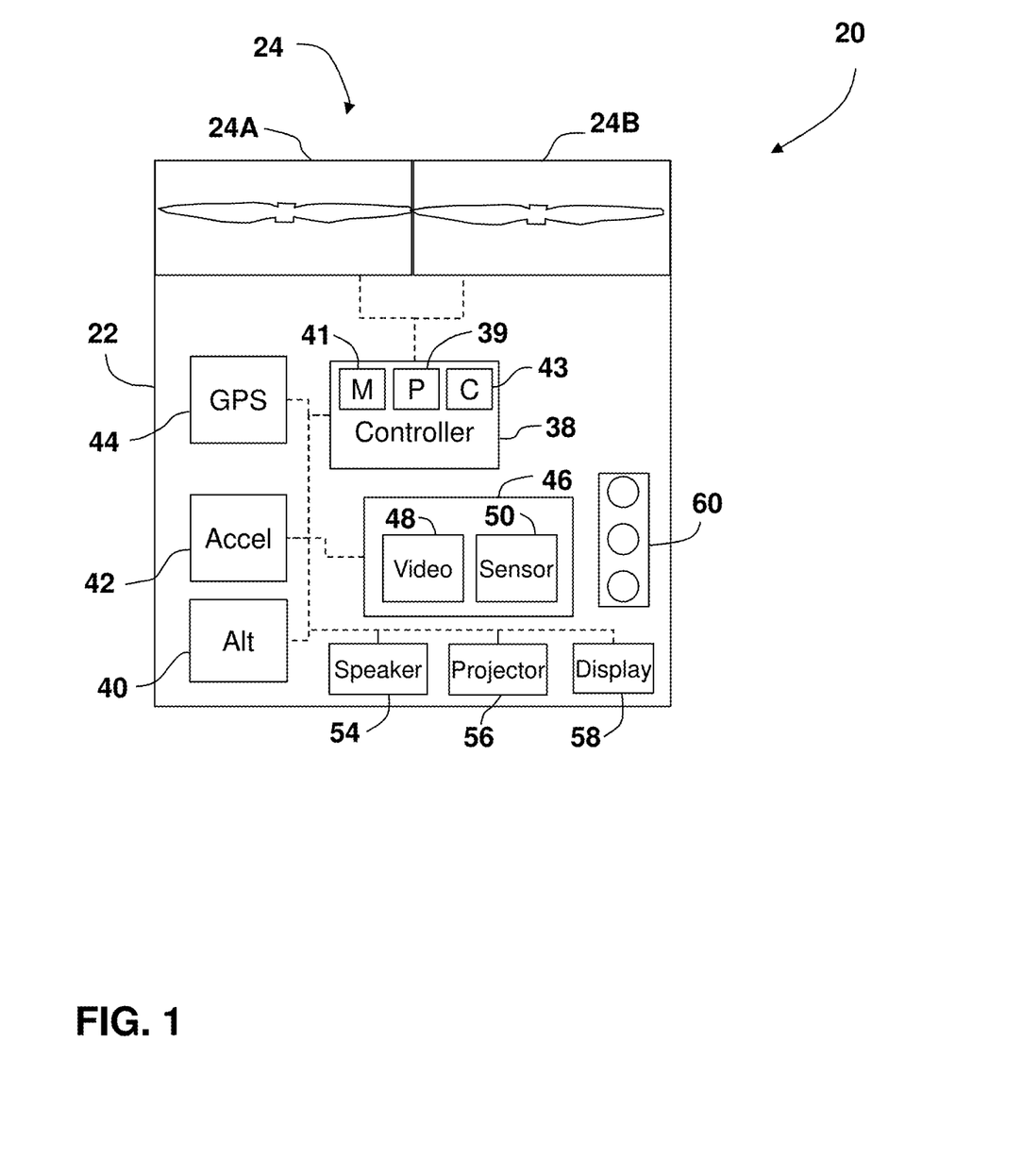
FIG. 1 depicts a block diagram of an unmanned aerial vehicle in accordance with one or more embodiments of this disclosure.

Referring now to FIG. 1, an embodiment is shown of a UAV 20. As used herein, the terms UAV or "drone" refer to an aerial vehicle capable to operating autonomously from a human operator to perform a predetermined function, such as perform monitoring functions for example. The UAV 20 includes a fuselage 22 that supports at least one thrust device 24. In one or more embodiments, the UAV 20 includes a plurality of thrust devices 24A, 24B, such as four thrust devices arranged about the periphery of the fuselage 22. In one or more embodiments, the thrust devices 24 include propeller member connected to a motor, either electric or internal combustion, which rotates to produce thrust. The thrust devices 24 may be configurable to provide both lift (vertical thrust) and lateral thrust (horizontal thrust). The vertical and horizontal components of the thrust allow the changing of the altitude (i.e. height), orientation and position of the UAV 20. In some embodiments, the orientation of the UAV 20 is with respect to the direction in which the UAV 20 pointing, with the feature 54 being the "front" or patient facing side of the UAV 20.

The UAV 20 includes a controller 38 having a processing circuit. The controller 38 may include processors that are responsive to operation control methods embodied in application code. These methods are embodied in computer instructions written to be executed by the processor, such as in the form of software. The controller 38 may further include additional circuits, such as but not limited to one or more processors 39, memory circuits 41 and communications circuits 43 for example. The communications circuit may be via a wireless communications medium. The wireless communications medium may include WiFi (e.g. IEEE 802.11), a Bluetooth® (e.g. IEEE 802.15.1 and its successors), RFID, near field communications (NFC), or cellular (e.g. LTE, GSM, EDGE, UMTS, HSPA and 3GPP cellular network technologies) for example.

The controller 38 is coupled to transmit and receive signals from the thrust devices 24 to determine and change their operational states (e.g. adjust lift from thrust devices 24, change the altitude, orientation and position of the UAV 20). The controller 38 may further be coupled to one or more sensor devices that enable to the controller to determine the altitude, orientation and position of the UAV 20. In one or more embodiments, these sensors may include an altimeter 40, a gyroscope or accelerometers 42 or a global positioning satellite (GPS) system 44. The controller 38 may use these input to operate the thrust devices 24 to move the UAV 20 to a predetermined altitude, orientation and position, and to maintain the UAV 20 in that altitude, orientation and position.

The UAV 20 may further include a patient sensor 46 that is used for monitoring the subject person. The patient sensor 46 may include one or more sensors, such as a video camera 48 for example. In some embodiments, the patient sensor 46 may include other sensors 50, such as but not limited to a microphone, 3D-camera (e.g. a time-of-flight camera), a 3D triangulation scanner (using either structured or unstructured light), a distance meter, a RADAR type device, a LIDAR type device, or a SONAR type device for example. In one or more embodiments, the plurality of sensors that make up the patient sensor 46 may be utilized individually, sequentially in time, or concurrently in various combinations with each other to determine if an episode of a movement disorder condition is occurring.

The patient sensors 46 may be used to determine motor characteristics associated with the subject patient. These sensors 46 may be used in cooperation with other systems, such as a wearable device for example, which is discussed further herein, to determine if the patient is experiencing an episode or a condition of their movement disorder such as FoG. As used herein, FoG is a condition experienced by some patients who have movement disorders (e.g. Parkinson's disease), when a FoG episode occurs their movement may be impaired or in some cases their body (or portions thereof) may freeze or fail to respond to the patient's desired movement. This is sometimes referred to as motor block. While the medical cause of FoG is not known, it has been found that presenting the patient with a gross sensory change stimulus, such as a pattern or a sound, may alleviate the episode and allow the patient to "unfreeze" and continue their movement.

It should be appreciated that while embodiments herein may refer to a particular movement disorder, such as Parkinson's disease, this is for exemplary purposes and the claimed invention should not be so limited. In other embodiments, the UAV 20 may be used to monitor any movement disorder that involves episodes for conditions such as FoG that respond to gross sensory change stimulus, such as but not limited to Wilson's disease, peripheral neuropathy, multiple sclerosis, chronic alcoholism, cerebellar damage, stroke, dementia, dementia with Lewy bodies, Alzheimer's disease, mercury intoxication, Hallevorden-Spatz disease, chorea, dystonias, ballismus, athetosis, dyskinesia, tic disorders, Tourette's syndrome, and fasciculation for example. Further, as used herein, the term "motor characteristic" refers to a measurement, or monitoring of the movement of the patient during the intentional performance of an act (e.g. walking, writing, moving an arm, etc.). As will be discussed herein, patients with movement disorders may at times have degraded or impaired motor characteristics due to an episode of a condition such as FoG that result in the patient's body stopping or holding in a semi-rigid position.

In one or more embodiments, the UAV 20 includes an audio speaker 54 that allows sounds, such as rhythmic sound for example, that may be played in the presence of the patient. It has been found that some music, such as music having a cadence above the patient's normal cadence (e.g. military marching music, or a metronome) are gross sensory stimuli that provides rhythmic auditory cues/change. In one or more embodiments, the audio stimulus may be a spoken voice of a motivational speaker that coaches the patient about movement. The introduction of the gross sensory change stimulus alleviates the FoG episode.

In one or more embodiments, the UAV 20 may include a projector 56, such as an LED, DLP or CRT type projector for example, that is configured to project one or more visual patterns onto a surface adjacent to the UAV 20. It has been found that visual cues or stimulus may also alleviate a FoG episode for a patient having a movement disorder. This visual patterns may include transverse lines on the floor, a moving spot of light (black, white or colored), tiled patterns, plaid patterns, fractal patterns, moving patterns, a pattern that moves as the patient moves, an image of a stairway with steps, parallel stripes and a laser line light beam projected on to the floor in front of the patient or a combination of the foregoing for example. The patterns may be projected directly in the patient's line of sight, or in their peripheral vision. In one embodiment, the visual pattern may be made by the UAV 20 rather than with the projector 56.

In one or more embodiments, the UAV 20 may include a display screen 58, such as an LCD or OLED display for example. The display screen 58 may provide visual stimulus similar to that described for the projector 56. In one or more embodiments, the UAV 20 may further include one or more light emitting diodes ("LED") 60 that emit a light. The LED's 60 may be modulated or sequenced to emit light in a pattern to provide a visual stimulus to alleviate the FoG episode.

Figure 2:
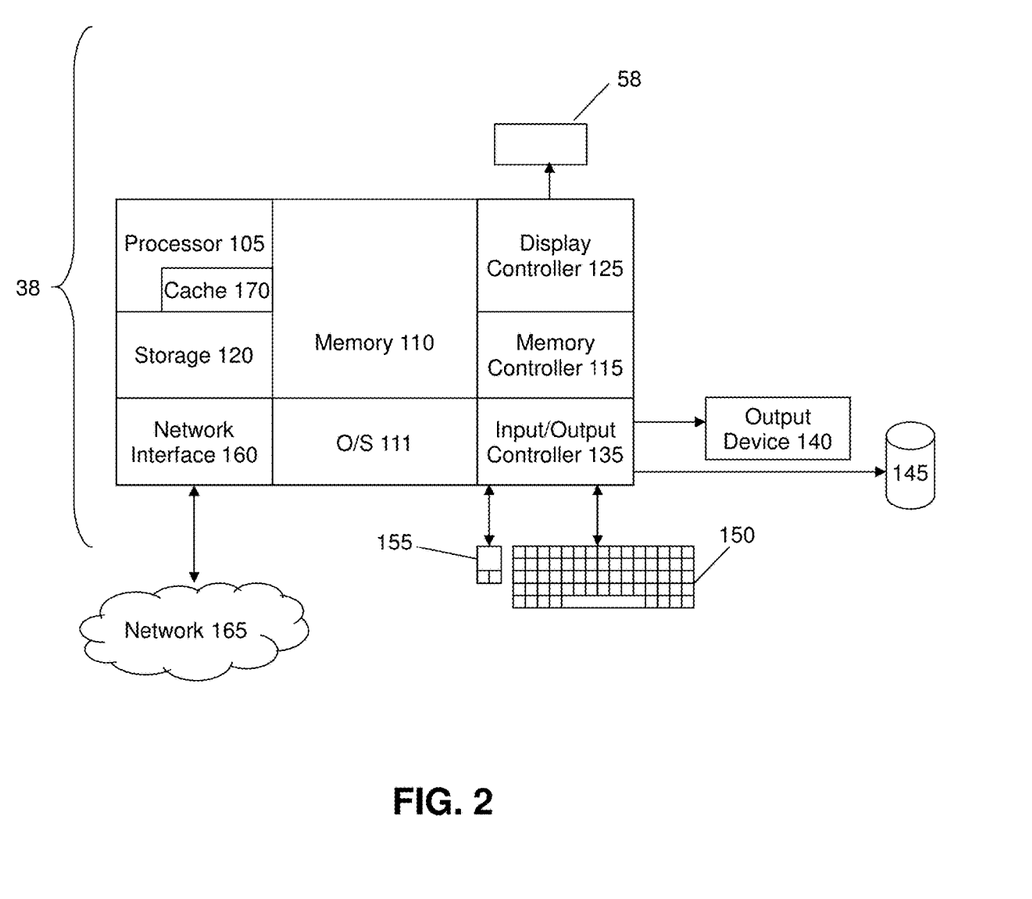
FIG. 2 depicts a block diagram of a controller for an unmanned aerial vehicle in accordance with one or more embodiments of this disclosure.

FIG. 2 illustrates a block diagram of an embodiment of controller 38 for use in implementing a system or method according to one or more embodiments. The systems and methods described herein may be implemented in hardware, software (e.g., firmware), or a combination thereof. In one or more embodiments, the methods described may be implemented, at least in part, in hardware and may be part of the microprocessor of a special or general-purpose controller, such as a personal computer, workstation, minicomputer, or mainframe computer.

In one or more embodiments, as shown in FIG. 2, the controller 38 includes a processor 105, memory 110 coupled to a memory controller 115, and one or more input devices 145 and/or output devices 140, such as peripheral or control devices that are communicatively coupled via a local I/O controller 135. These devices 140 and 145 may include, for example, battery sensors, position sensors, accelerometers, cameras, video cameras, microphones, audio speakers, projectors, LEDs and the like. Input devices such as a conventional keyboard 150 and mouse 155 may be coupled to the I/O controller. The I/O controller 135 may be, for example, one or more buses or other wired or wireless connections, as are known in the art. The I/O controller 135 may have additional elements, which are omitted for simplicity, such as controllers, buffers (caches), drivers, repeaters, and receivers, to enable communications.

The I/O devices 140, 145 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 105 is a hardware device for executing hardware instructions or software, particularly those stored in memory 110. The processor 105 may be a custom made or commercially available processor, a central processing unit (CPU), an auxiliary processor among several processors associated with the controller 38, a semiconductor based microprocessor (in the form of a microchip or chip set), a macroprocessor, or other device for executing instructions. The processor 105 includes a cache 170, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 170 may be organized as a hierarchy of more cache levels (L1, L2, etc.).

The memory 110 may include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 110 may incorporate electronic, magnetic, optical, or other types of storage media. Note that the memory 110 may have a distributed architecture, where various components are situated remote from one another but may be accessed by the processor 105.

The instructions in memory 110 may include one or more separate programs, each of which comprises an ordered listing of executable instructions for implementing logical functions. In the example of FIG. 2, the instructions in the memory 110 include a suitable operating system (O/S) 111. The operating system 111 essentially may control the execution of other computer programs and provides scheduling, input-output control, file and data management, memory management, and communication control and related services.

Additional data, including, for example, instructions for the processor 105 or other retrievable information, may be stored in storage 120, which may be a storage device such as a hard disk drive or solid state drive. The stored instructions in memory 110 or in storage 120 may include those enabling the processor to execute one or more aspects of the systems and methods of this disclosure.

Systems and methods according to this disclosure may be embodied, in whole or in part, in computer program products or in controller 38, such as that illustrated in FIG. 2. The controller 38 may further include a display controller 125 coupled to a user interface or display 58. In one or more embodiments, the display 58 may be an LCD screen. As discussed in more detail herein, the display 130 may be used for communicating with the patient, such as to provide instructions or displaying a visual pattern. In one or more embodiments, the controller 38 may further include a network interface 160 for coupling to a network 165. The network 165 may be an IP-based network for communication between the controller 38 and an external server, client and the like via a broadband connection. The network 165 transmits and receives data between the controller 38 and external systems. In one or more embodiments, the external system may be the UAV 20, wherein the transmitting and receiving of data allows the controller 38 to determine when an episode of a movement disorder condition is occurring. In one or more embodiments, the network 165 may be a managed IP network administered by a service provider. The network 165 may be implemented in a wireless fashion, e.g., using wireless protocols and technologies, such as WiFi, WiMax, satellite, etc. The network 165 may also be a packet-switched network such as a local area network, wide area network, metropolitan area network, the Internet, or other similar type of network environment. The network 165 may be a fixed wireless network, a wireless local area network (LAN), a wireless wide area network (WAN) a personal area network (PAN), a virtual private network (VPN), intranet or other suitable network system and may include equipment for receiving and transmitting signals.

Figure 3A:
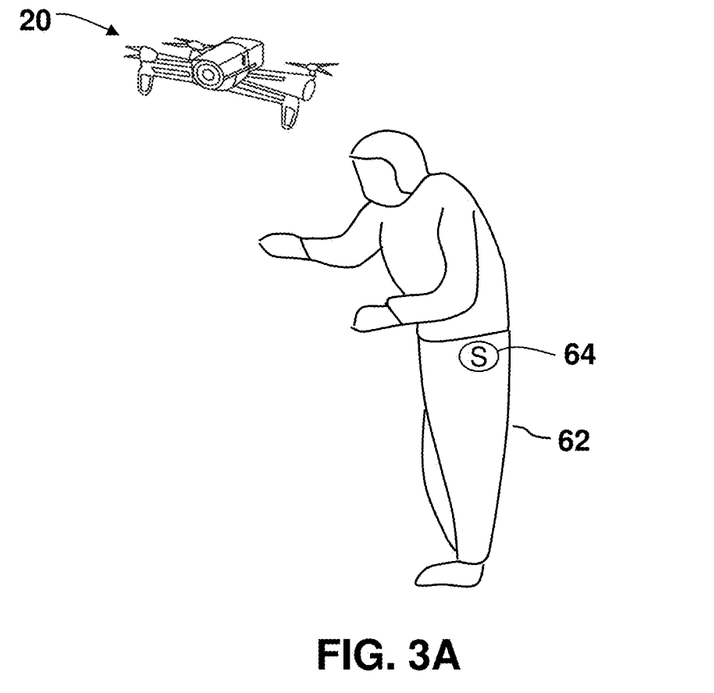
FIG. 3A and FIG. 3B depict a view of unmanned aerial vehicle monitoring and projecting a gross sensory change stimulus for a patient in accordance with one or more embodiments of this disclosure.
Figure 3B:
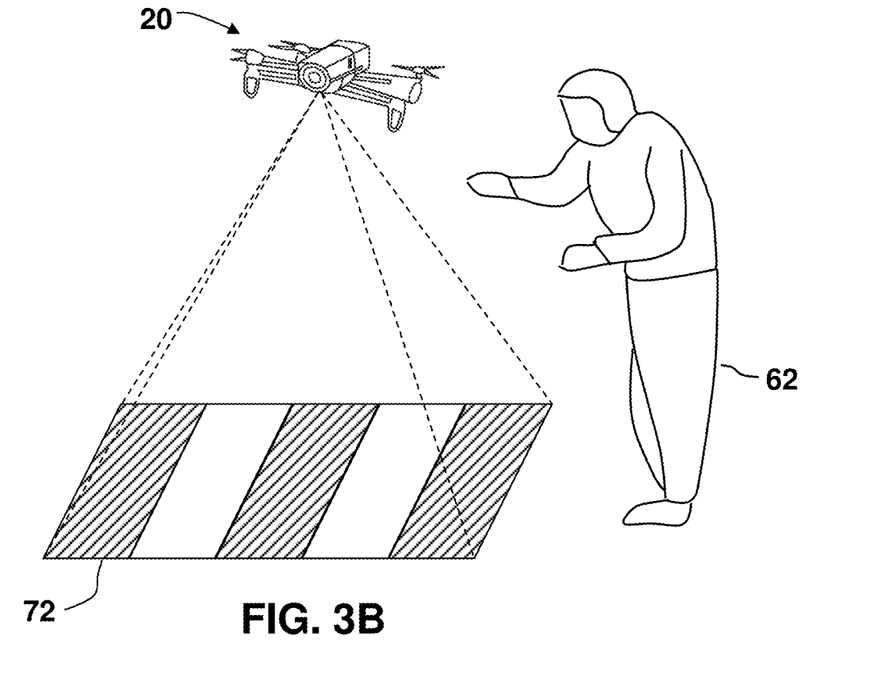
Figure 4A:
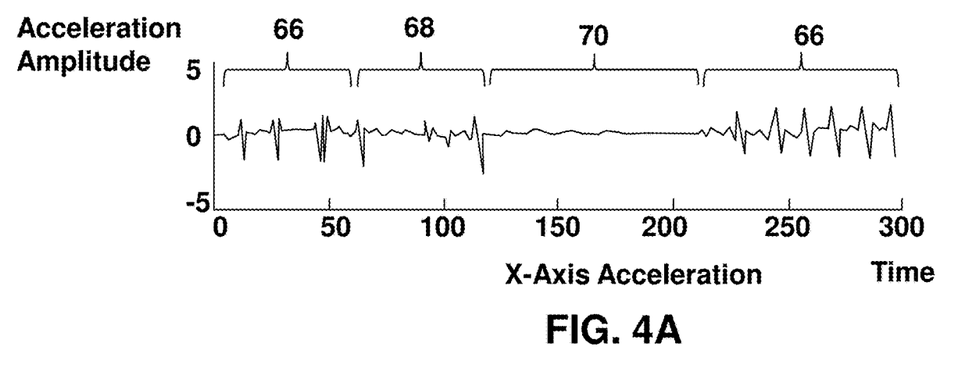
FIG. 4A, FIG. 4B and FIG. 4C depict a plot of an exemplary acceleration vs time relationship as measured by an accelerometer coupled to or worn by the patient.
Figure 4B:
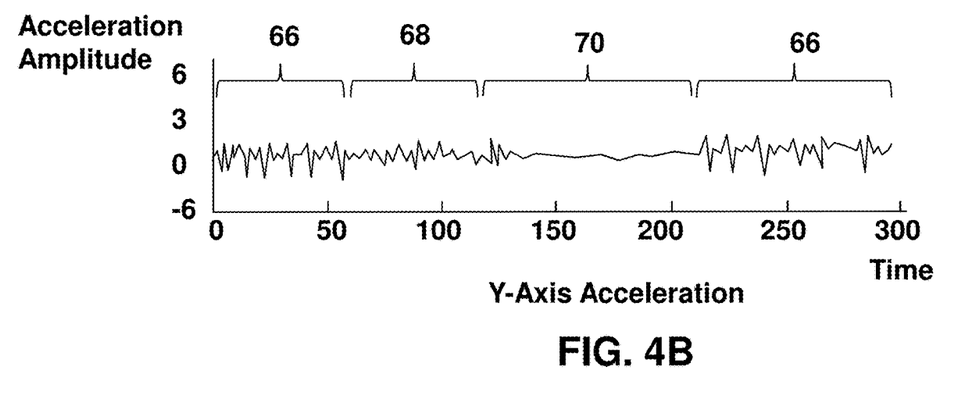
Figure 4C:
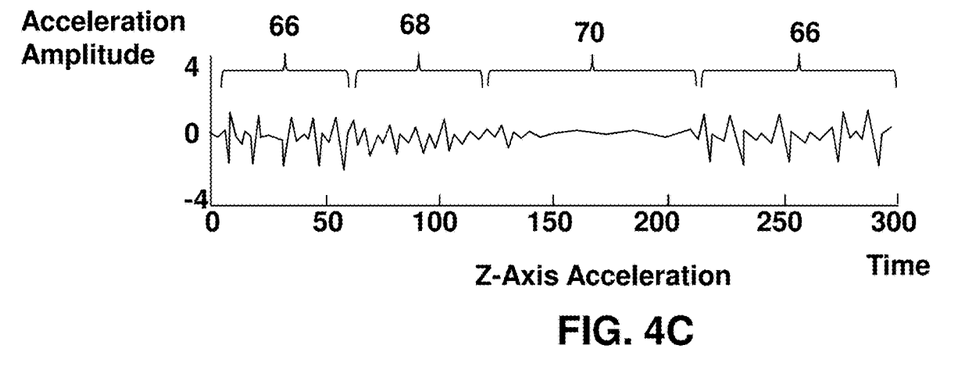

Referring now to FIG. 3A and FIG. 3B, with continuing reference to FIG. 1, an embodiment is shown for monitoring, detecting and alleviating an episode of a movement disorder condition, such as FoG for example. In one or more embodiments, the patient 62 has measurable motor characteristics that may be used to determine the occurrence of an episode that is impairing or inhibiting the movement of patient 62. In one or more embodiments, the motor characteristics may be measured using a wearable device 64 having a sensor (e.g. an accelerometer, inertial measurement unit (IMU), electromyography (EMG), electroencephalography (EEG), electrocardiography (ECG), or other wearable devices that monitors physiological states). An example of an accelerometer measurement is shown in FIGS. 4A-4C for each axis of a tri-axial accelerometer that is measuring the patient 62 while they are walking. It should be noted that from the accelerometer measurements, the state of the patient 62 may be determined as having a normal walking state 66, a pre-FoG state 68 (characterized by reduced acceleration amplitudes), and a FoG state 70 (characterized by little or no acceleration amplitude). In one or more embodiments, the wearable device 64 may also provide haptic feedback to the patient, such as to alert them to that an episode of a movement disorder condition may occur in the near future (e.g. when they are in the pre-FoG state 68).

Figure 5A:
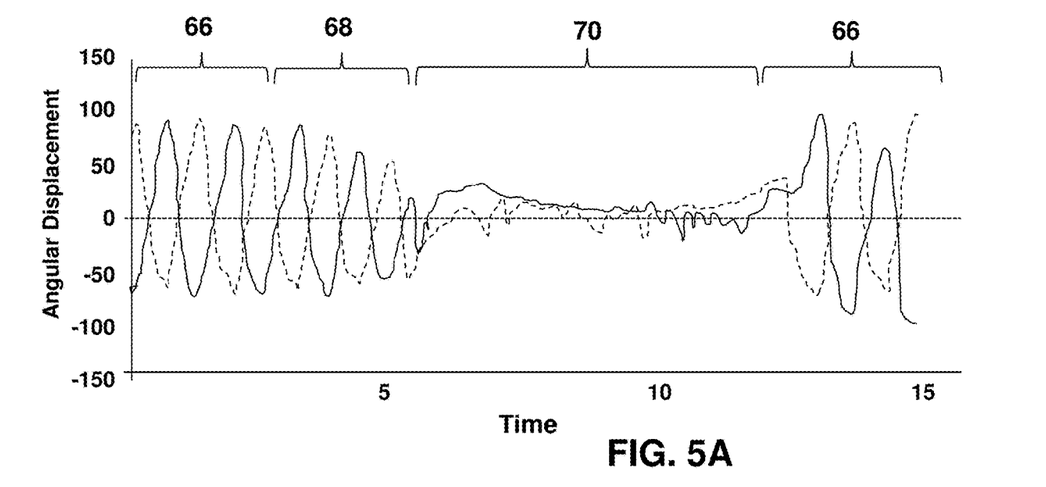
FIG. 5A depicts a plot of an exemplary angular displacement vs time relationship of a patient's legs.
Figure 5B:
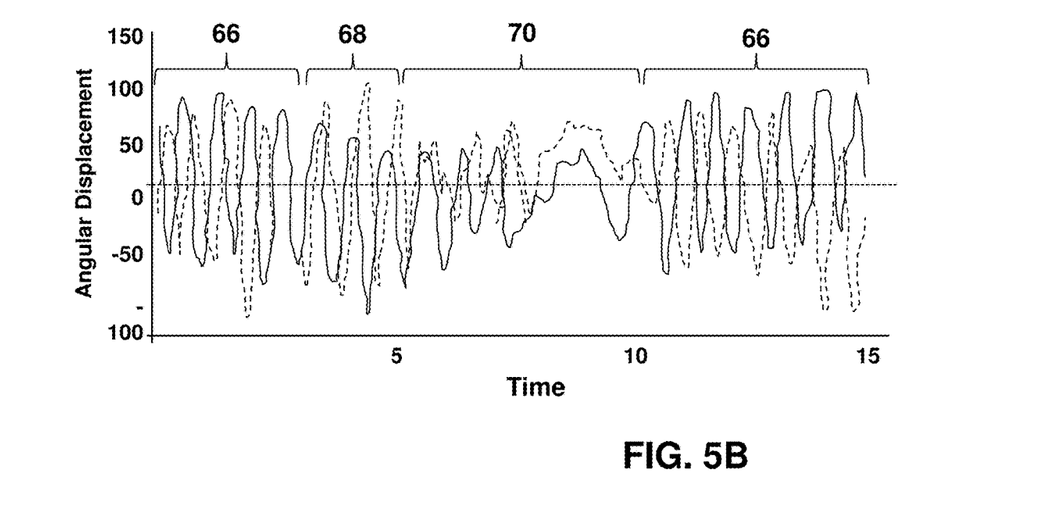
FIG. 5B depicts a plot of an exemplary angular displacement vs time relationship of a patient's finger.

It should be appreciated that other types of motor characteristic measurements may also be made that allow for the determination of the walking, pre-FoG and FoG states. As shown in FIG. 5A, a leg displacement measurement is shown wherein the walking state 66 is characterized by a rhythmic signal having a substantially level amplitude. As the patient 62 enters a pre-FoG state 68, the amplitude of the displacement signal steadily decreases until reaching the FoG state 70 where the amplitude of the displacement signal becomes erratic. It should be appreciated that while embodiments herein refer to the FoG episode as affecting the patient's legs, this is for exemplary purposes and the claimed invention should not be so limited. The motor characteristic measurement may also be of other parts or sections of the patient's body. For example, FIG. 5B illustrates an exemplary displacement signal for a sensor on the patient's finger (e.g. a wearable device such as a ring). Similarly, the normal function state 66, pre-FoG state 68 and FoG state 70 may be characterized from the amplitude and waveform of the displacement signal. It should be appreciated that other wearable devices may also be used, such as but not limited to pressure sensors in the patient's footwear or socks for example.

As shown in FIG. 3A, in one or more embodiments the patient 62 is monitored by one or more sensors 64 that measure motor characteristics that may be used to detect an episode of a movement disorder condition (e.g. FoG). The sensors 64 may communicate directly with the UAV 20 via a wireless communications medium, such as by radio signal (e.g. Bluetooth, WiFi). In other embodiments, the sensors 64 may communicate with a controller (not shown) worn by the patient, such as the patient's cellular phone or other mobile computing device for example. In still other embodiments, the sensors 64 may communicate with one or more remotely located computing devices. The patient worn controller or the remote computing devices may perform an intermediary role and perform some or all of the diagnostic methods described herein in the determination of the occurrence of an episode of a movement disorder condition and the initiation of an intervention by the UAV 20 may be determined by the wearable controller, the remote computing device, the controller 38 or a combination of the foregoing. As used herein, the phrase "remotely located" means that the devices, components or objects are spatially separated from each other. Devices, components or objects that are remotely located may be located in the same room, the same building, the same geographic region or geographic regions that are distal from each other.

In one or more embodiments, a gait irregularity of the patient 62 may be determined by performing a fast Fourier transform (FFT) on the signal from the sensor(s) 64. In one or more embodiments, the FFT output is separated into predetermined frequency bands. In one or more embodiments, the output of the FFT in predetermined or defined spectral bands are compared to predetermined values or ratio of values across the spectral bands. In one or more embodiments, the gait irregularity may be determined by comparing a ratio of the average amplitude or power of a high frequency FFT band to the average amplitude or power of low frequency band a predetermined threshold value for example. The predetermined threshold value may be established based on a value determined by a medical professional, a value determined by the patient, or from typical values used by the patient's cohort or demographic group for example.

It should be appreciated that the measurement of the motor conditions and the determination of an episode of a movement disorder condition may be made using the sensors 46, such as with video camera 48 using image analysis techniques (e.g. measuring movement between frames). In one or more embodiments where the UAV 20 includes measurement sensors, such as a 3D triangulation scanner or a 3D camera for example, the movement of the patient 62 may be analyzed and the measurement of the motor conditions and the occurrence of an episode of the movement disorder condition determined.

In one or more embodiments, when the occurrence of an episode of the movement disorder condition is determined, the UAV 20 projects or emits a gross sensory change stimulus ("GSCS"). In one or more embodiments, the GSCS may be a visual pattern 72 or an audio sound such as a high cadence music. In one or more embodiments, the GSCS may be a combination of visual patterns, audio patterns (e.g. a metronome), rhythmic sounds, or music.

In one or more embodiments, the GSCS may be a visual pattern formed or performed by the UAV 20. The UVA 20 may form the pattern through an image printed on the fuselage 22, or the emitting of light from LED's 60 for example. The UAV 20 may form the pattern through an image (e.g. stripes) printed on the thrust devices 24. The UAV 20 may further perform the pattern by flying in a pattern sequence (e.g. a figure eight). In one or more embodiments, the UAV 20 may be configured with a printed pattern and simultaneously move in a predetermined pattern sequence.

It should be appreciated that while the embodiments herein include the monitoring of the patient 62 for a FoG episode due to Parkinson's disease, this is for exemplary purposes and the claimed invention should not be so limited. In other embodiments, other motor characteristics of the patient 62 may be monitored for the occurrence of episodes for conditions such as akinesia, cerebral palsy, multiple sclerosis, and Alzheimer's disease for example. Some of the monitoring or determination may be performed with the assistance of medical personnel such as a nurse for example. For example, the medical personnel may monitor the patient via the video camera 48 and transmit a signal to the UAV 20 to initiate the projecting or emitting of the GSCS.

The projection of the visual pattern 72 onto the pathway, ground or floor near the patient 62 may be affected by the surface conditions (e.g. obstructions, obstacles, texture, color, roughness, etc.) of the ground or floor. In one or more embodiments, prior to projecting the visual pattern 72, the UAV acquires an image of the ground or floor and determines the visual pattern 72 based at least in part on the surface condition. For example, the color, arrangement, size or shape of the visual pattern 72 may be changed based at least in part on the surface condition of the ground or floor.

It should further be appreciated that while one or more embodiments herein describe the use of a single UAV 20, this is for exemplary purposes and the claimed invention should not be so limited. In other embodiments, a plurality of UAV's 20 may cooperate to provide desired monitoring of the patient. For example, while a first UAV 20 is maintaining a position adjacent the patient 62, another UAV 20 may be recharging or refueling. Further, multiple UAV 20 may cooperate to project or emit the GSCS to create more complex patterns or sounds.

Figure 6:
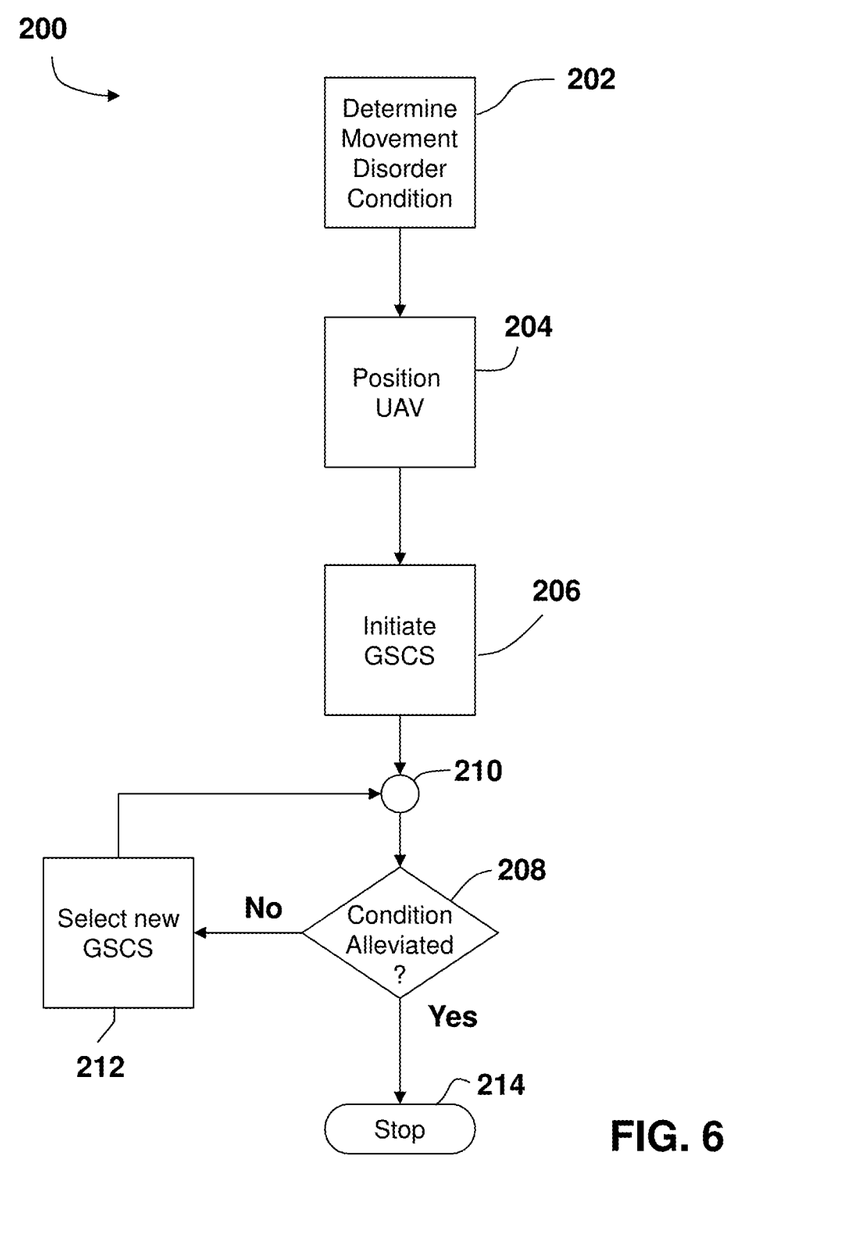
FIG. 6 depicts a flow diagram of a method of determining and alleviating an episode of a condition in a patient with a movement disorder in accordance with one or more embodiments of this disclosure.

Referring now to FIG. 6, a method 200 is shown for determining the occurrence of and the alleviating of an episode of a movement disorder condition that utilizes a UAV 20. The method 200 begins in block 202 where occurrence of an episode of a movement disorder condition such as FoG is determined. In one or more embodiments, the determination of the episode of the movement disorder condition is based at least in part on the measurement of motor characteristics by sensors disposed on or worn by the patient 62. In one or more embodiments, the determination of the episode of the movement disorder condition is based at least in part on the non-contact measurement of motor characteristics by sensors 46 on the UAV 20, such as but not limited to video camera 48 for example. In one or more embodiments, the determination of the movement disorder condition may be based at least in part on a detecting of a patient activation, such as through a verbal command by the patient 62 that is received by a microphone on the UAV 20. In one or more embodiments, the determination of the episode of the movement disorder condition is based at least in part on the patient cohort, such as based on demographics, age group, location, cultural background or other medical conditions to which the patient is grouped or classified for example. In one or more embodiments, the determination of the episode of the movement disorder condition is based at least in part on the medications taken by the patient 62, the time frame in which the patient last took their medication or the when the next dosage of the medication is scheduled to be administered. In one or more embodiments, the determination of the episode of the movement disorder condition is based at least in part on receipt of a signal from medical personnel or other third parties (e.g. a caretaker or family member). In one or more embodiments, the determination of the episode of the movement disorder condition may be based at least in part on previous episode occurrences of the movement disorder condition and motor characteristic measurements made during those episode occurrences.

In one or more embodiments, upon detection of the episode of the movement disorder condition a signal may be transmitted to medical personnel, a caretaker, or one or more other designated persons. In some instances, the occurrence of the episode of the movement disorder condition may result in the patient falling. In one or more embodiments, the signal may be electronic (e.g. an email or cellular text message), audio or visual (e.g. flashing of LED's 60)

After determining that the episode of the movement disorder condition is potentially occurring, the method 200 proceeds to block 204 where the UAV 20 is positioned adjacent the patient 62. In one or more embodiments, the UAV 20 may be follow or be continuously present with the patient 62. Thus the positioning of the UAV 20 involves moving and reorienting the UAV 20 to project or emit the GSCS to the desired location. In one or more other embodiments, the UAV 20 may be located a predetermined location, such as at a recharging/refueling station or centrally located within the facility/building that the patient is located for example. In these embodiments, the UAV 20 determines a route to the location of the patient and travels from the predetermined location to the location of the patient. In these embodiments, the patient 62 may carry a device for tracking the location of the patient 62 and this location is transmitted to the UAV 20 when the occurrence of the episode of the movement disorder condition is determined.

When the UAV 20 is positioned in the desired location relative to the patient 62, the method 200 proceeds to block 206 where the UAV 20 initiates the displaying, projecting or emitting of the GSCS, such as a visual pattern 72, a sound pattern or a combination of the foregoing for example. In one or more embodiments, the visual pattern 72 may be projected onto the ground in front of the patient 72. In one or more embodiments, the visual pattern 72 is projected onto a surface in the patient's peripheral vision. In one or more embodiments, the UAV 20 may move to generate a moving visual pattern. In one or more embodiments, the UAV 20 and the GSCS may change based on direct coupling to measurement of the patient movement and a transformation of the movement into a change signal. In this way, the system may make use of a closed loop feedback system. The control system then makes use of objectives surrounding the alleviation of the movement disorder.

In an embodiment, the UAV 20 may also provide audio or visual instructions to the patient 62 in addition to projecting the GSCS. For example, the UAV 20 may project a visual cue (e.g. a stripe on the floor) and then provide audio (via speaker 54) or visual (via display 58) instructions that encourage the patient 62 to step over the visual cue to allow them to resume motion.

The method 200 then proceeds to query block 208 where it is determined whether the episode has been alleviated. For example, in an instance where the movement disorder condition is FoG, the episode is alleviated when the patient 72 is able to move or is "unfrozen." In one or more embodiments, the method 200 may include a time delay block 210 wherein the GSCS is displayed, projected or emitted for a predetermined amount of time before the determination of query block 208. In one or more embodiments, when the query block 208 returns a negative, the method 200 proceeds to block 212 where a new GSCS is selected (or combination of GSCS) and displayed, projected or emitted in an attempt to alleviate the episode of the movement disorder condition. The method 200 then loops back to block 210. When the query block 208 returns a positive, the method 200 proceeds to block 214 where the method 200 terminates.

Figure 7:
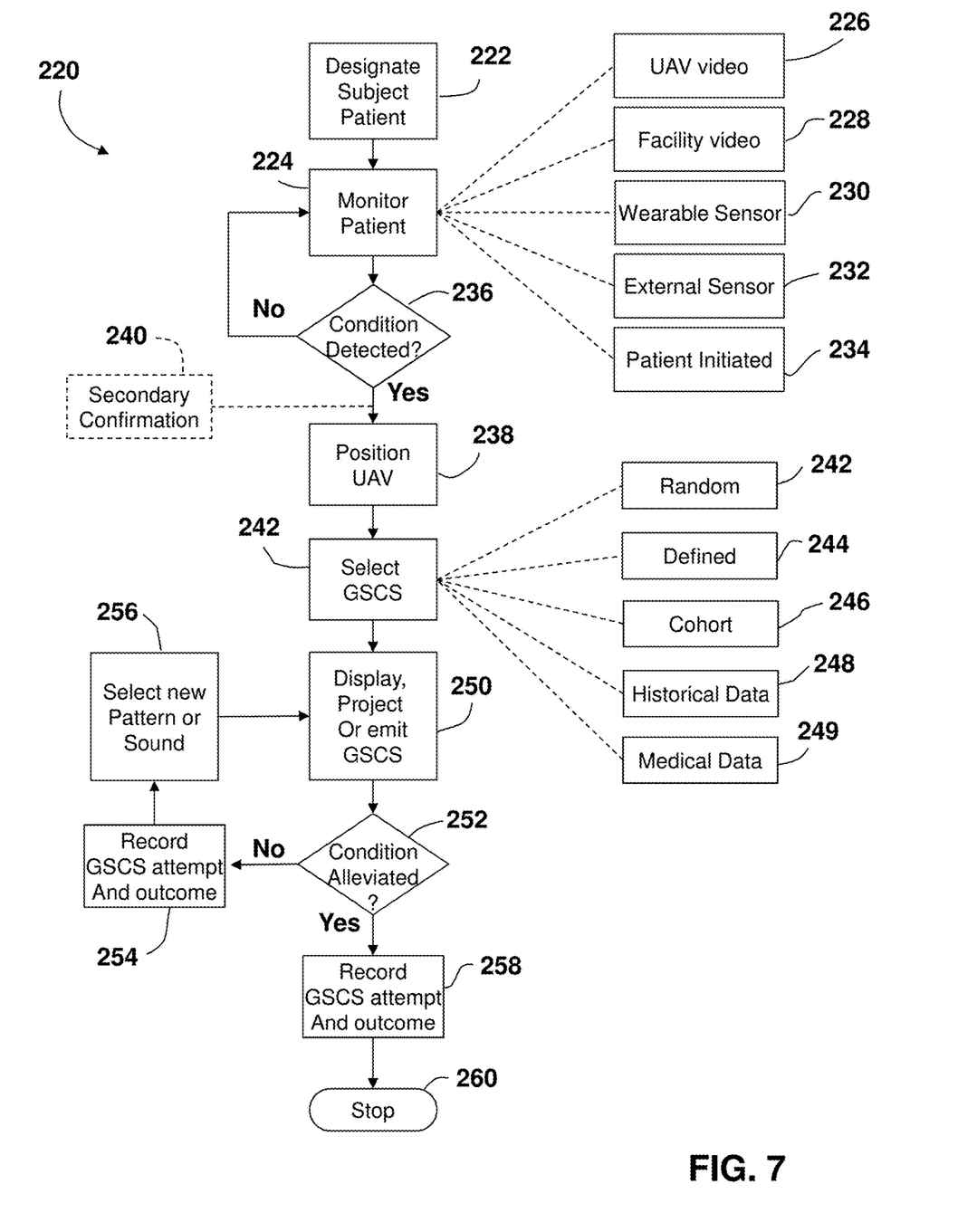
FIG. 7 depicts a flow diagram of a method of determining and alleviating an episode of a condition in a patient with a movement disorder in accordance with one or more embodiments of this disclosure.

Referring now to FIG. 7, another method 220 is shown for alleviating an episode of the movement disorder condition in a patient with the use of a UAV 20. The method 220 begins in block 222 where the patient is designated and is monitored in block 224. The monitoring may be performed using the video camera on the UAV 226, a video camera in the facility or building in which the patient is located 228, one or more wearable sensors 230, external sensors 232 (e.g. a sensor such as an accelerometer, inertial measurement unit (IMU) or load cell attached to a walker or cane), a patient initiated monitoring, 234 or a combination of the foregoing for example.

The method 220 then proceeds to block 236 where it is determined if an episode of the movement disorder conditions is detected. When the query block 236 returns a negative, the method 220 loops back to block 224 and the monitoring of the patient 62 continues. When the query block 236 returns a positive, the method 220 proceeds to block 238 where the UAV 20 is positioned relative to the patient 62. In one or more embodiments, the method 220 may include an optional secondary confirmation in block 240. The secondary confirmation provides a separate and independent confirmation that an episode of the movement disorder condition is occurring. For example, where the episode is detected based on signals from a wearable sensor, images from the video camera 48 may be used to confirm (either using image analysis such as movement between frames of the acquired video images, or by manual review with medical personnel) that the patient 62 is not moving for example.

When the UAV 20 is in the desired position, the method 220 proceeds to block 242 where the GSCS, such as a displayed pattern, a projected pattern, an emitted sound or a combination of the foregoing for example, is selected. The selection of the GSCS may be based on a random selection 244 of a plurality of predetermined patterns or sounds, selected from a defined ordered list 246 of predetermined patterns or sounds, selected based on the cohort 248 in which the patient 62 is grouped, selected based on historical data 250, or selected based on medical data 249 (e.g. medications taken and time to next dosage). As discussed in more detail herein, in one or more embodiments, the effectiveness (or lack thereof) of the GSCS in alleviating the episode may be stored and tracked and used during future occurrences in the selection of a GSCS. In one or more embodiments, machine learning methodologies use the patient historical data and other data (e.g. cohort data) in the selection of the GSCS.

Once the GSCS is selected, the method proceeds to block 250 where the GSCS is displayed, projected or emitted (or a combination thereof). As discussed herein the GSCS may be applied for a predetermined period of time and the method 220 proceeds to query block 252. In query block 252, it is determined if the episode of the movement disorder condition has been alleviated. This determination may be ascertained using the same means as was used to detect the occurrence of the episode in the first place, namely video images, wearable sensors and the like for example. When the query block 252 returns a negative, meaning the episode continues to afflict the patient 62, then the method 220 proceeds to block 254 where the attempted intervention with the GSCS is recorded. In one or more embodiments, other relevant conditions (e.g. time of day, food eaten, medication taken, lighting conditions, number of other people present) may be recorded and stored in memory. As discussed herein, in one or more embodiments, the recorded attempts and other relevant data may be utilized in the selection of future GSCS.

The method 220 then proceeds to block 256 where a new GSCS is selected. In the selection of the new GSCS, the first GSCS is eliminated and the new GSCS may be selected from the remaining predetermined GSCS (or combinations thereof). In one or more embodiments, the selection may be based on machine learning, for example the new GSCS may be selected based on it being effective in the past when the first GSCS was ineffective in alleviating the episode. The method 220 then loops back to block 250 and displays, projects or emits the second GSCS.

When the query block 252 returns a positive, meaning the episode of the movement disorder condition was alleviated, the method 220 proceeds to block 258 and the success of the intervention by the GSCS is recorded and stored in memory. In one or more embodiments, other relevant data (e.g. time of day, food eaten, medication taken, lighting conditions, the number of other people present or their density) may also be recorded and stored in memory. The method 220 then proceeds to block 260 where the method stops.

Figure 8:
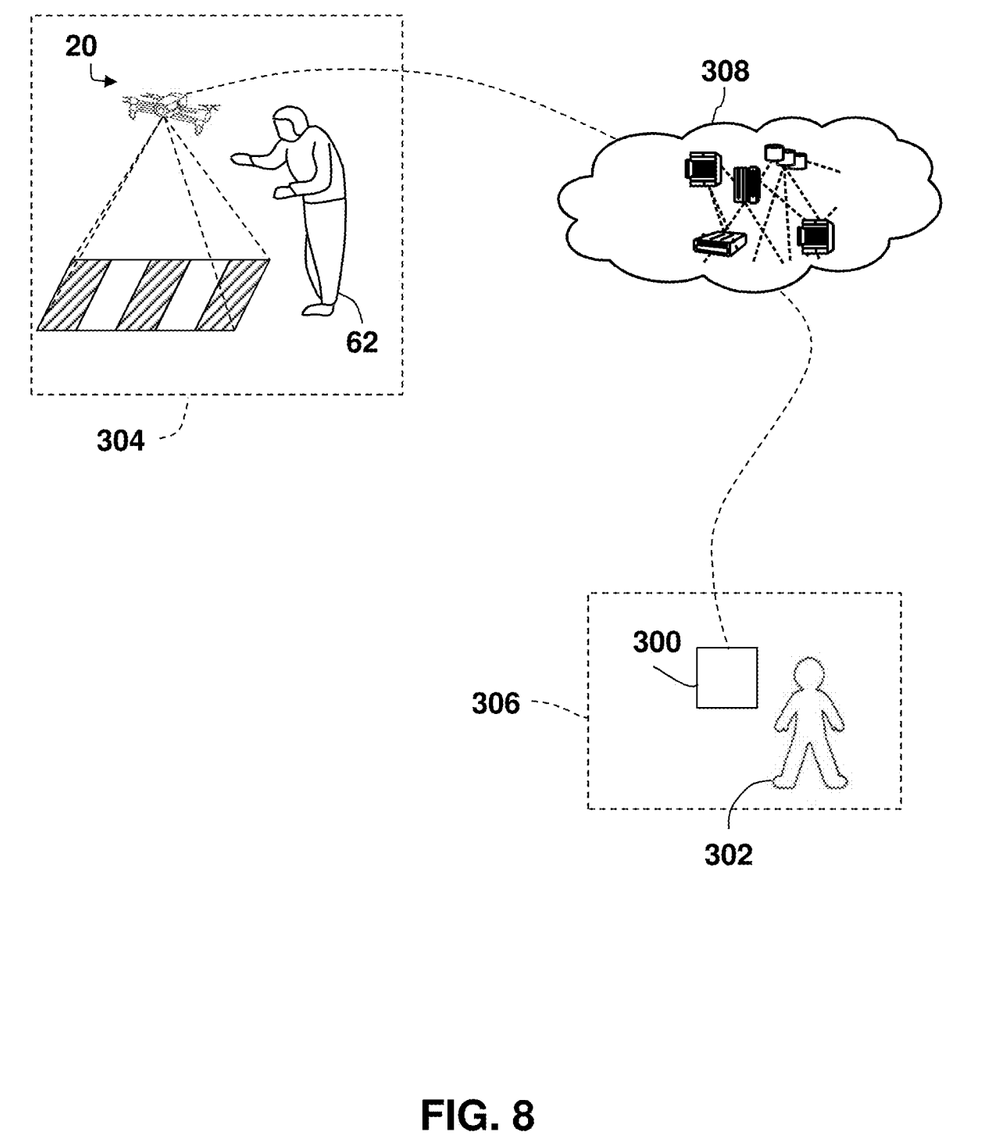
FIG. 8 depicts a schematic view of a remote treatment of a patient by a doctor in accordance with one or more embodiments of this disclosure.

While the embodiments of FIGS. 3-7 described the operation of the UAV 20 acting in an autonomous manner, this is for exemplary purposes and the claimed invention should not be so limited. Referring now to FIG. 8, an embodiment is shown where the UAV 20 operates at least partially based on commands received by a medical personnel 302 (e.g. a physician). In this embodiment, it is contemplated that the patient 62 is in a first location 304 (e.g. their home) and the medical personnel 302 are in a second location 306 (e.g. medical office) where the second location 306 is remotely located from the first location 304. It should be appreciated that in one or more embodiments the patient 62 and medical personnel 302 may be located in the same but different parts of the same facility or medical campus.

In this embodiment, the UAV 20 may be connected for communication via a network 308 that allows for transmission bidirectional signals between a computer 300 operated by the medical personnel 302 and the UAV 20. The network 308 may be a LAN, a WAN, a PAN, an intranet, or the Intranet for example. The UAV 20 in response to a signal from the medical personnel 302 displays, projects or emits a GSCS in an attempt to alleviate the episode of the movement disorder condition. In one or more embodiments, the medical personnel may see the measured motor characteristics in real time or near real-time. In one or more embodiments, the medical personnel 302 may observe the patient 62 via the video camera 48. In one or more embodiments, the medical personnel 302 may speak to the patient 62 via an audio speaker and microphone on the UAV 20. In this embodiment, the medical personnel 302 may change the GSCS displayed, projected or emitted from the UAV 20. Thus, in this embodiment, the UAV may operate in a semi-autonomous mode of operation, with the medical personnel controlling the evaluation.

In one or more embodiments, the UAV 20 may store or receive data or information from one or more remote computers. Further, some or all of the evaluation of the motor characteristic measurements and the determination of the occurrence of an episode of the movement disorder condition may be performed on the UAV 20, performed by a controller carried by the patient (e.g. a cellular phone or mobile computing device), performed on one or more remote computers, or a combination of the foregoing. For example, the determination of whether a movement disorder is indicated (block 202, FIG. 6) may be performed by a computing device remotely located from the UAV 20. In one embodiment, a cloud computing environment may cooperate with the UAV 20 in the detection of and the alleviating of an episode of the movement disorder condition.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 9:
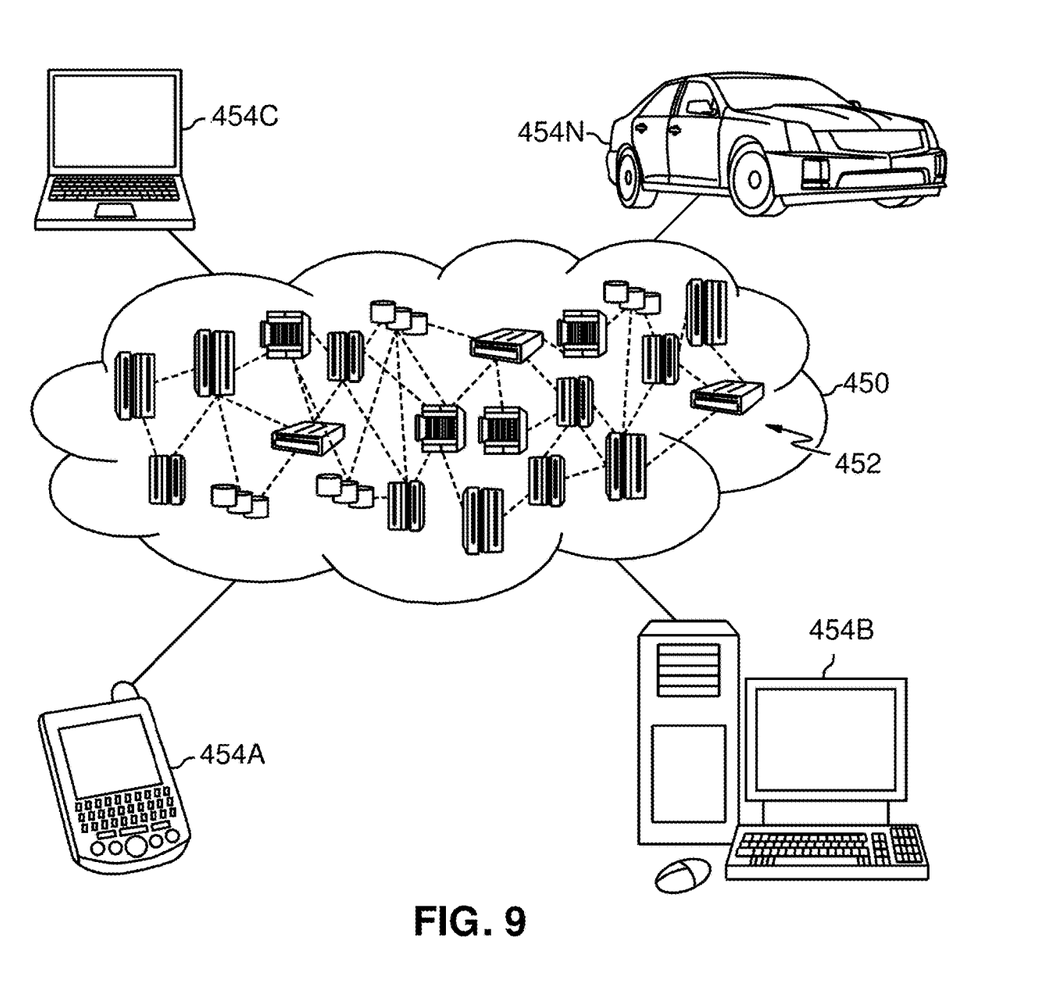
FIG. 9 depicts a cloud computing environment according to one or more embodiments of the present invention.

Referring now to FIG. 9, illustrative cloud computing environment 450 is depicted. As shown, cloud computing environment 450 comprises one or more cloud computing nodes 452 with which local computing devices used by cloud consumers, such as, for example, personal digital assistant (PDA) or cellular telephone 454A, desktop computer 454B, laptop computer 454C, and/or automobile computer system 454N may communicate. Nodes 452 may communicate with one another. They may be grouped (not shown) physically or virtually, in one or more networks, such as Private, Community, Public, or Hybrid clouds as described hereinabove, or a combination thereof. This allows cloud computing environment 450 to offer infrastructure, platforms and/or software as services for which a cloud consumer does not need to maintain resources on a local computing device. It is understood that the types of computing devices 454A-N shown in FIG. 9 are intended to be illustrative only and that computing nodes 452 and cloud computing environment 450 can communicate with any type of computerized device over any type of network and/or network addressable connection (e.g., using a web browser).

Figure 10:
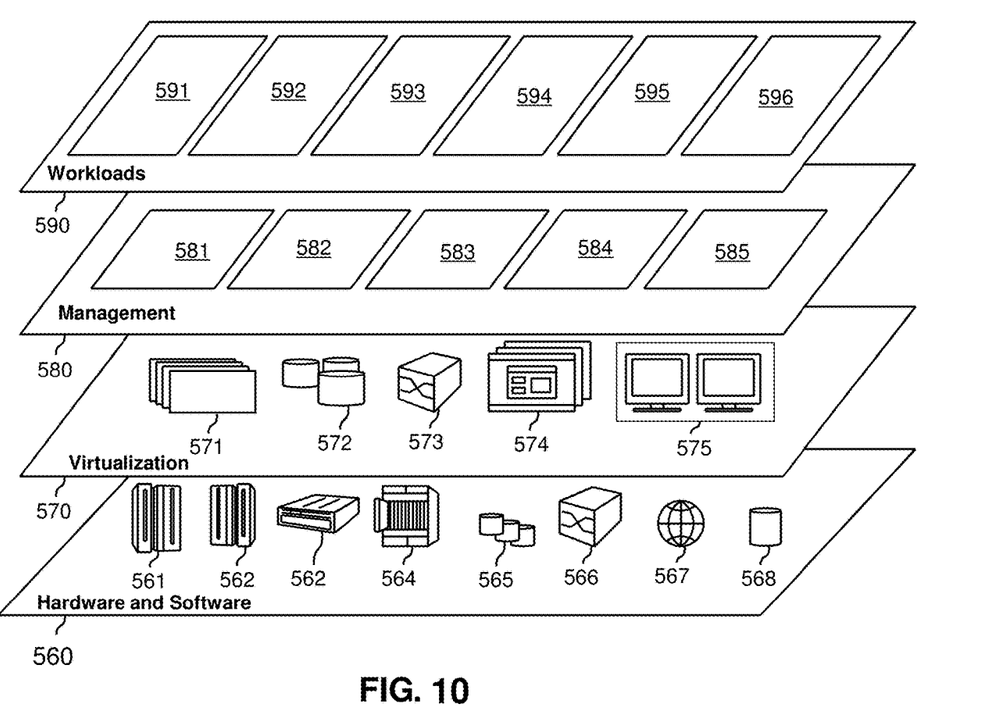
FIG. 10 depicts abstraction model layers according to one or more embodiments of the present invention.

Referring now to FIG. 10, a set of functional abstraction layers provided by cloud computing environment 450 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572; virtual networks 573, including virtual private networks; virtual applications and operating systems 574; and virtual clients 575.

In one example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provides pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: mapping and navigation 591; software development and lifecycle management 592; virtual classroom education delivery 593; data analytics processing 594; transaction processing 595; and a movement disorder management 596. The movement disorder management 596 may perform one or more methods that allow for determination of the occurrence of an episode of the movement disorder condition, selection of the GSCS and the display, projection or emitting of the GSCS using a UAV, such as but not limited to the methods described in reference to FIG. 6 and FIG. 7 for example.

Technical effects and benefits of one or more embodiments include using a gross sensory change stimulus to alleviate a episode for a patient having a movement disorder using an aerial vehicle.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   deploying an unmanned aerial vehicle (UAV) to a location of a patient based on an occurrence of an episode of a movement disorder condition, the episode of the movement disorder condition comprising a freezing of gait of the patient;
   selecting with a processor a first gross sensory change stimulus comprising a pattern or sound;
   projecting from the UAV the first gross sensory change stimulus;
   attempting to alleviate the episode of the movement disorder condition based at least in part on the projecting of the first gross sensory change stimulus from the UAV; and
   detecting when the episode of the movement disorder condition is alleviated based on a movement of the patient indicating that the patient is no longer experiencing the freezing of gait episode.

2. The method of claim 1, further comprising detecting the occurrence of the episode of the movement disorder condition, wherein the determining the occurrence of the episode of the movement disorder condition includes measuring a motor characteristic with a sensor, the sensor being operably coupled to the patient.

3. The method of claim 2, wherein the first gross sensory change stimulus is changed based on a continuous measurement of the motor characteristic with the sensor via a closed loop feedback system.

4. The method of claim 1, wherein the first gross sensory change stimulus is selected from a group consisting of: a visual pattern projected on a surface, a visual pattern displayed on a display coupled to the UAV, a visual pattern formed by the UAV, a rhythmic sound, and a spoken voice.

5. The method of claim 1, further comprising determining a surface conditions and obstacles in a pathway of the patient and adjusting the first gross sensory change stimulus based at least in part on the surface conditions and obstacles.

6. The method of claim 1, further comprising recording an outcome of the projecting of the first gross sensory change stimulus in alleviating the episode of the movement disorder condition.

7. The method of claim 1, further comprising selecting a second gross sensory change stimulus based on the projecting of the first gross sensory change stimulus and the episode of the movement disorder condition not being alleviated within a predetermined period of time.

8. The method of claim 1, wherein the first gross sensory change stimulus is a combination of a visual pattern and a rhythmic sound.

9. The method of claim 2, wherein the detecting of the occurrence of the episode of the movement disorder condition includes performing a fast Fourier transform on a signal received from the sensor and comparing an output of the fast Fourier transform in defined spectral bands to a predetermined values or a ratio of outputs values compared across spectral bands.

10. The method of claim 1, further comprising providing haptic feedback to the patient with a wearable device based at least in part on transmitting a signal from the UAV to the wearable device.

11. The method of claim 1, further comprising providing audio instructions by the UAV to the patient to step over the first gross sensory change stimulus, wherein the first gross sensory change stimulus is a pattern projected onto a ground in front of the patient.

12. The method of claim 1, wherein the projecting of the first gross sensory change stimulus include forming a visual pattern with the UAV.

13. The method of claim 2, further comprising transmitting a signal with the UAV to a remotely located computer based on the determining the occurrence of the episode of the movement disorder condition.

* * * * *